United States Patent [19]

Britton et al.

[11] Patent Number: 5,226,434

[45] Date of Patent: Jul. 13, 1993

[54] DENTAL FLOSS INCORPORATING CONTROLLED-RELEASE THERAPEUTIC AGENTS

[76] Inventors: Raymond L. Britton, 6146 Olympia Dr., Houston, Tex. 77057; Constantine Armeniades, 2127 Addison Rd., Houston, Tex. 77030

[21] Appl. No.: 770,904

[22] Filed: Oct. 4, 1991

[51] Int. Cl.$^5$ .............................................. A61C 15/00
[52] U.S. Cl. ..................................... 132/321; 132/329
[58] Field of Search ................................ 132/321, 329

[56] References Cited

U.S. PATENT DOCUMENTS

| | | | |
|---|---|---|---|
| 4,986,288 | 1/1991 | Kent et al. | 132/321 |
| 5,098,711 | 3/1992 | Hill et al. | 424/401 |

Primary Examiner—Gene Mancene
Assistant Examiner—Cindy A. Cherichetti

[57] ABSTRACT

A strip of dental floss that is capable of receiving and retaining a substantially solid coating is coated with an ingestible binder that is capable of being stripped from the dental floss by the mechanical forces of flossing and being deposited in situ in the interproximal region of the teeth. The binder incorporates a medicament, particularly being an antibacterial agent such as chlorhexidine that is slowly released from the binder over a predetermined period of time responsive to oral fluid and oral temperature. This invention accomplishes delivery of the medicament to specific areas of the teeth where plaque build-up is likely to occur and minimizes staining of the teeth by the antibacterial agent.

6 Claims, No Drawings

DENTAL FLOSS INCORPORATING CONTROLLED-RELEASE THERAPEUTIC AGENTS

FIELD OF THE INVENTION

This invention relates generally to the treatment of periodontal disease through the use of antibacterial agents such as chlorhexidine and more particularly to such treatment by time release of antibacterial agents which are incorporated within a dental floss carried binder and applied to the teeth and gingiva during flossing.

BACKGROUND OF THE INVENTION

Periodontal disease affects the supporting tissues of the teeth, bone, periodontal ligament, cementum and gingiva. It is periodontal disease which causes a great percentage of all tooth loss in adults.

The reason for periodontal disease is bacterial plaque accumulation on the tooth surfaces. Over the years, chlorhexidine digluconate 0.2% and 0.12% mouthrinses have shown to be most effective in controlling bacterial plaque accumulation when used twice daily. However, a significant side effect of its use is tooth staining, which depends in great proportion on the dietary habits of the individual. Consequently, plaque removal is mainly achieved through the use of mechanical means during regular oral hygiene.

The most difficult areas to reach for proper oral hygiene are the interproximal surfaces of the teeth. These areas are best cleaned with the aid of dental floss. The various types of dental floss used in the prior art effect only a mechanical cleaning of the interproximal tooth areas. Antibacterial medications, such as chlorhexidine are typically dispensed to the teeth and gums by means of periodic mouth rinsing with appropriate solutions of the medication. This treatment method has two drawbacks: it exposes the entire tooth surface to the discoloring action of chlorhexidine. It also achieves only transient concentrations of the medication, which remain high only for a brief period after rinsing, and decay rapidly as the medication is carried away by the saliva. It is desirable therefore to provide an oral system that permits delivery of the medication to the interproximal surfaces of the teeth particularly at the juncture of the enamel and gingival tissues, wherein such medicament delivery is continuous for a significantly long period of time.

SUMMARY OF THE INVENTION

The present invention makes it possible to incorporate chlorhexidine (or other medications) onto the surface of dental floss or other tooth cleaning implements. The medication is incorporated within inert carrier particles, which are stripped from the dental floss by the mechanical action of its normal use and deposited at the interproximal tooth surfaces. There, they release the medication at a controlled rate as the binding carrier is slowly dissolved by the saliva.

The present invention brings the following advantages to the treatment and prevention of periodontal disease: it achieves a most efficient utilization of the medication by depositing it only at the interproximal tooth surfaces, where it is most needed; it achieves a most effective utilization of the medication by controlling its rate of release, so that adequate concentrations are maintained locally over several hours after flossing.

In addition, in the case of chlorhexidine, by limiting its deposition to the interproximal tooth surfaces as opposed to rinsing the whole mouth, the present invention reduces considerably the tooth discoloration, which is an undesirable side effect of this medication.

DETAILED DESCRIPTION OF PREFERRED EMBODIMENT

This invention comprises two sequential processes: (a) incorporation of the therapeutic agent into the carrier system for controlled release, and (b) coating of the floss (or other tooth cleaning implements) with the therapeutic-agent/carrier system in a manner that will facilitate their deposition on the interproximal tooth surfaces

(a) CONTROLLED-RELEASE CARRIER

The carrier system for the therapeutic agent in this invention consists of a porous hydrated mineral, such as bentonite or similar clays. These materials are readily available in the form of fine particles (10–50m in size) with a highly porous surface The particle structure consists of crystalline metal oxide layers, separated by layers of hydration water, which may comprise up to 20% of the mineral. When the clay particles are mixed with aqueous or alcoholic solutions of chlorhexidine or other bioactive agents, the solutions are readily absorbed into the porous particles and may partially replace the hydration water of the mineral.

The extent of this absorption and the tenacity with which the chlorhexidine is held into the mineral structure depends to a large extent on the temperature and pressure at which the process takes place. If the chlorhexidine solution is mixed with the clay at ambient temperatures and atmospheric pressures, it is held very lightly and will be released readily when the clay becomes immersed in saliva during the application of this invention. However, if the clay particles are pretreated by heating in the range of 65°–80° C. and exposure to partial vacuum (0.1–0.4 bars absolute pressure) the chlorhexidine becomes more tightly bound to the clay and its subsequent release into the saliva is significantly slowed down. In this manner the pretreatment of the clay carrier particles is used to control the rate of medication release when the medicated particles are deposited in the interproximal tooth surfaces by the flossing process.

(b) FLOSS COATING BINDERS

The medicated clay particles are coated onto the floss by means of a binder. This binder must be ingestible and easily stripped from the floss (or other tooth cleaning implement) by the mechanical action of its use. Gelatin USP (plain or flavored) or similar proteinaceous compounds and admixtures thereof used in accordance with Government Standards are excellent carriers. However, other substances that meet the above requirements (such as edible gums, confections and other compounds and those suitable for use as agents in preparations acceptable for food or pharmaceutical use) may be used with equal effectiveness.

EXAMPLE 1

Carrier System

A 25% (by weight) solution of chlorhexidine in methanol was prepared by mixing the components at ambient temperature. The chlorhexidine solution was placed in a separatory funnel. Purified (research grade) bentonite having a particle size range of from 10-50 m was placed in a container (glass flask) with heating and stirring arrangements. The chlorhexidine solution and bentonite containers were connected to each other and to a vacuum mixing system. The vacuum mixing system that was used included a glass flask having a magnetic stirring bar with a flask heater and magnetic stirrer. The bentonite was placed within the flask and heated with the magnetic stirrer in continuous operation. A glass separatory funnel, containing the chlorhexidine solution, with a stopcock at its lower end, was coupled to the flask by a funnel connector tube extending through a stopper of the flask so that upon opening of the stopcock the chlorhexidine solution would flow by gravity and by vacuum into the flask. The flask incorporated a vacuum line having a three-way valve for selectively communicating the flask to vacuum through the vacuum line or to vent the flask to the atmosphere.

Equal amounts of the chlorhexidine solution and bentonite were used in this preparation. The bentonite was heated to 60° C. and subjected to a partial vacuum (0.2 bars absolute pressure) for 25-30 minutes. At the end of this period the connection to the vacuum system was closed and the separatory funnel stopcock was opened, allowing the chlorhexidine solution to mix with the bentonite. The bentonite and chlorhexidine components formed a paste. When the mixing was complete the methanol was removed by reexposing the bentonite container to partial vacuum.

Binder System

A 5% by weight solution of gelatin in water was prepared by mixing the ingredients and heating to 85°-90° C. Other inert ingredients, such as saccharine for sweetening or special flavors can be added as desired at this point.

Coating Suspension

This was prepared by mixing 30% by weight carrier particles with warm gelatin (ca. 60° C.) to form a fluid suspension. The clay has a tendency to settle and should be kept in suspension by stirring.

Coating Procedure

The floss was coated with warm suspension (ca 50° C.) using various procedures known in the prior art. It should be noted that the temperature of the suspension affects its fluidity, ease of application and appearance and consistency of the final coating. The speed of the coating process should be adjusted so that the floss acquires a continuous coating of an average thickness that is ca. 20% of the floss diameter.

The above process incorporates onto the floss a coating which releases 75% of its chlorhexidine content within one hour of exposure to saliva and 99% within four hours.

EXAMPLE 2

This process differs from Example 1 only in the treatment of the bentonite used in the carrier system. The bentonite was heated to 80° C. All other conditions remained the same as set forth above in Example 1. The above process incorporates onto the floss a coating which releases 42% of its chlorhexidine content within one hour of exposure to saliva, 68% after four hours, and 99% after eight hours.

EXAMPLE 3

This process differed from Examples 1 and 2 only in that the carrier system was prepared by mixing bentonite with the chlorhexidine/methanol solutions at ambient conditions without heating or evacuation. The above process results in a coating that releases 98% of its chlorhexidine content within the first hour of exposure to saliva.

One method that was found suitable for preparing a therapeutic dental floss incorporating an antibacterial medicament having chlorhexidine in the range of from 2-3 parts by weight, water in the range of from 83-84 parts by weight, ethyl alcohol of 14 parts by weight and bentonite. The binder for this paste medicament included gelatin in the range of 4 parts by weight, water in the range of 96 parts by weight and a flavor and sweetening agent. The binder was heated to a temperature where the binder becomes fluid and was mixed with the antibacterial agent to form a coating mixture. The coating mixture was extruded about a strand of dental floss and was cooled to ambient temperature at which point the coating became substantially solid. The completed dental floss was then wound about a spool for subsequent use.

Another medicament was prepared by utilizing the same chemical constituents as set forth above In this case the chlorhexidine was mixed with water and alcohol at ambient temperature to form a chlorhexidine solution. The bentonite clay was desiccated over $P_2O_5$ at 40°-60° C. for a minimum of 24 hours. The desiccated bentonite clay was then mixed with equal amounts of the chlorhexidine solution to form a mixture. This mixture was then dried at a temperature range of from 40°-60° C.

In view of the foregoing, it is evident that the present invention is one well adapted to attain all of the objects and features hereinabove set forth, together with other objects and features which are inherent in the apparatus disclosed herein.

As will be readily apparent to those skilled in the art, the present invention may be produced in other specific forms without departing from its spirit or essential characteristics. The present embodiment, is therefore, to be considered as illustrative and not restrictive, the scope of the invention being indicated by the claims rather than the foregoing description, and all changes which come within the meaning and range of the equivalence of the claims are therefore intended to be embraced therein.

What is claimed is:

1. Therapeutic dental floss, comprising:
    (a) a strip dental floss capable of receiving and retaining a substantially solid coating;
    (b) an ingestible binder forming a substantially continuous coating on said dental floss and capable of being stripped from said dental floss by the mechanical forces of flossing and being deposited in situ especially in the interproximal region defined by the juncture of the enamel of the teeth and the gingival tissues;
    (c) a medicament being incorporated within said ingestible binder and being released from said ingestible binder over a predetermined period of time responsive to oral fluid and oral temperature, thus providing for time released delivery of said medicament to oral tissue such as the sulcular pockets and sub-gingival tissue structure for prevention and therapy of caries and periodontal disease, wherein, said ingestible binder is bentonite clay in the form of a fine powder having a particulate size range of 5-50 m.

2. The therapeutic dental floss of claim 1, wherein: said medicament has a range of concentration to provide minimum content for desired anti-bacterial action and maximum content that avoids toxic effects when ingested.

3. Therapeutic dental floss, comprising:
(a) a strip dental floss capable of receiving and retaining a substantially solid coating;
(b) an ingestible binder forming a substantially continuous coating on said dental floss and capable of being stripped from said dental floss by the mechanical forces of flossing and being deposited in situ especially in the interproximal region defined by the juncture of the enamel of the teeth and the gingival tissues; and
(c) a medicament being incorporated within said ingestible binder and being released from said ingestible binder over a predetermined period of time responsive to oral fluid and oral temperature, thus providing for time released delivery of said medicament to oral tissue such as the sulcular pockets and sub-gingival tissue structure for prevention and therapy of caries and periodontal disease;
wherein
(a) said medicament includes
(1) an anti-bacterial agent;
(2) water;
(3) ethyl alcohol; and
(4) bentonite; and
(b) said binder includes
(1) gelatin
(2) water; and
(3) flavor and sweetener(s).

4. The therapeutic dental floss of claim 3, wherein said anti-bacterial agent is chlorhexidine.

5. The therapeutic dental floss of claim 3, wherein said coating is a suspension in the range of 5-60% by weight of said carrier.

6. Therapeutic dental floss, comprising:
(a) a strip dental floss capable of receiving and retaining a substantially solid coating:
(b) an ingestible binder forming a substantially continuous coating on said dental floss and capable of being stripped from said dental floss by the mechanical forces of flossing and being deposited in situ especially in the interproximal region defined by the juncture of the enamel of the teeth and the gingival tissues; and
(c) a medicament being incorporated within said ingestible binder and being released from said ingestible binder over a predetermined period of time responsive to oral fluid and oral temperature, thus providing for time released delivery of said medicament to oral tissue such as the sulcular pockets and sub-gingival tissue structure for prevention and therapy of caries and periodontal disease,
wherein,
(a) said medicament includes

|     |                       | Parts by weight |
|-----|-----------------------|-----------------|
| (1) | chlorhexidine         | 2-3;            |
| (2) | water                 | 83-84;          |
| (3) | ethyl alcohol         | 14; and         |
| (4) | bentonite (purified); and |             |

(b) said binder includes:

|     |                       | Parts by weight |
|-----|-----------------------|-----------------|
| (1) | gelatin               | 4;              |
| (2) | water                 | 96; and         |
| (3) | flavor and sweetener(s). | [as needed.] |

* * * * *